United States Patent
Quick et al.

(10) Patent No.: US 11,156,530 B2
(45) Date of Patent: Oct. 26, 2021

(54) SYSTEM AND METHOD FOR MECHANICAL SYSTEM CHIP DETECTION CAPABILITY VERIFICATION

(71) Applicant: Textron Innovations Inc., Providence, RI (US)

(72) Inventors: Steven R. Quick, Hurst, TX (US); Cyrus Elliott Rahimzadeh, Arlington, TX (US)

(73) Assignee: TEXTRON INNOVATIONS INC., Providence, RI (US)

( * ) Notice: Subject to any disclaimer, the term of this patent is extended or adjusted under 35 U.S.C. 154(b) by 142 days.

(21) Appl. No.: 16/579,446

(22) Filed: Sep. 23, 2019

(65) Prior Publication Data

US 2021/0088409 A1 Mar. 25, 2021

(51) Int. Cl.
| | | |
|---|---|---|
| *G01M 13/02* | (2019.01) | |
| *F01M 11/10* | (2006.01) | |
| *F16H 57/04* | (2010.01) | |
| *F16N 29/00* | (2006.01) | |

(52) U.S. Cl.
CPC ............ *G01M 13/02* (2013.01); *F01M 11/10* (2013.01); *F16H 57/0405* (2013.01); *F16N 29/00* (2013.01)

(58) Field of Classification Search
CPC ..... G01M 13/02; F16H 57/04; F16H 57/0405
See application file for complete search history.

(56) References Cited

U.S. PATENT DOCUMENTS

| | | | |
|---|---|---|---|
| 4,692,698 A | 9/1987 | Lewis | |
| 6,459,995 B1* | 10/2002 | Collister | G01N 27/221 702/23 |
| 7,151,383 B2* | 12/2006 | Itomi | G01N 33/2888 324/698 |
| 8,421,486 B2* | 4/2013 | Akiyama | G01N 27/02 324/698 |
| 2004/0123644 A1* | 7/2004 | Jakoby | F01M 11/10 73/19.11 |
| 2009/0084171 A1* | 4/2009 | Kauffman | G01M 15/042 73/114.55 |
| 2010/0109686 A1 | 5/2010 | Zhe et al. | |
| 2011/0153275 A1* | 6/2011 | Satake | G01N 21/534 702/184 |

(Continued)

FOREIGN PATENT DOCUMENTS

FR 3016043 A1 7/2015

*Primary Examiner* — Eric S. McCall
(74) *Attorney, Agent, or Firm* — Slater Matsil, LLP

(57) ABSTRACT

A system and method for verifying a mechanical system chip detection capability, the method including determining a slurry injection location in machinery according to a targeted obstruction in the machinery in relation to a target chip detector of the machinery, placing an injection tube through a machinery casing of the machinery, providing a slurry tube connected to the injection tube, the slurry tube containing a slurry comprising conductive chips and a lubricant, operating the machinery until the machinery meets one or more predetermined operating parameters, injecting the slurry into the machinery casing during operation of the machinery and after the machinery meets the one or more predetermined operating parameters, and monitoring the target chip detector for detection of the conductive chips during the operation of the machinery.

20 Claims, 9 Drawing Sheets

(56) References Cited

U.S. PATENT DOCUMENTS

| | | | |
|---|---|---|---|
| 2011/0265569 A1* | 11/2011 | Ganji | F16C 33/6688 |
| | | | 73/587 |
| 2013/0160549 A1* | 6/2013 | Nissen | G01N 29/032 |
| | | | 73/572 |
| 2015/0047419 A1* | 2/2015 | Cao | G01N 33/2888 |
| | | | 73/53.07 |
| 2015/0192558 A1* | 7/2015 | De Coninck | G01N 33/2888 |
| | | | 73/61.49 |
| 2015/0346181 A1* | 12/2015 | Isenberg | G01N 33/2888 |
| | | | 73/114.55 |

* cited by examiner

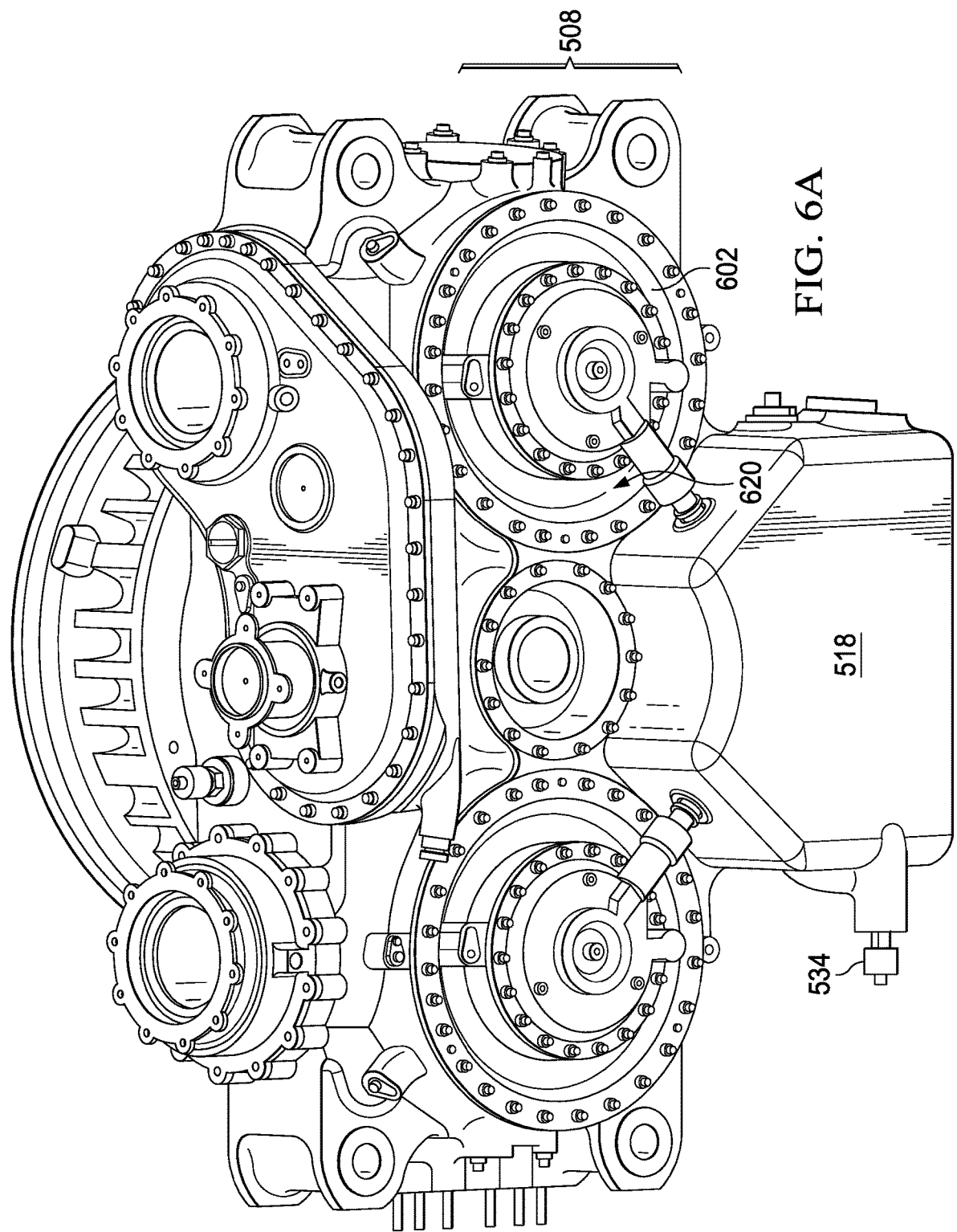

SYSTEM AND METHOD FOR MECHANICAL SYSTEM CHIP DETECTION CAPABILITY VERIFICATION

TECHNICAL FIELD

The present invention relates generally to a system and method for testing a chip detection system, and, in particular embodiments, to a system and method for providing a non-destructive metal chip detection test for a mechanical system.

BACKGROUND

Generally, complex machinery include high precision power transmission mechanisms. In particular, for vehicles such as aircraft, ships, rotorcraft, and the like, and for industrial machinery, heavy equipment, or other powered equipment, complex power distribution systems such as transmissions, gear drives, or the like may be used to control and distribute mechanical force or power generated at a central power provision point. For example, for a rotorcraft, one or more centrally located engines may power a main rotor, a tail rotor, an electrical generating unit, hydraulic systems, and the like. One more transmissions, gearboxes or similar power transmission systems may be provided to transfer mechanical movement or power from the engines to the desired outputs to drive the relevant elements.

In many cases, mechanical power is transferred using a mechanical transmission having gears, bearing, chains, belts, or the like. The use of such mechanical transmission elements allows for predictable engineering and system design, but requires the interaction of hard surfaces that are prone to wear. One system for monitoring the wear on these internal transmission elements is a chip detection system that detects conductive particles or chips in the lubricant used within the mechanical system.

SUMMARY

An embodiment method includes determining a slurry injection location in machinery according to a targeted obstruction in the machinery in relation to a target chip detector of the machinery, placing an injection tube through a machinery casing of the machinery, providing a slurry tube connected to the injection tube, the slurry tube containing a slurry comprising conductive chips and a lubricant, operating the machinery until the machinery meets one or more predetermined operating parameters, injecting the slurry into the machinery casing during operation of the machinery and after the machinery meets the one or more predetermined operating parameters, and monitoring the target chip detector for detection of the conductive chips during the operation of the machinery.

An embodiment method includes injecting conductive chips into a mechanical system at an injection location in the mechanical system during operation of the mechanical system and when the mechanical system is at a normal operating parameter, monitoring a target chip detector of the mechanical system for detection of the conductive chips during operation of the mechanical system, determining a detection time that is a time between injection of the conductive chips and detection of one or more of the conductive chips by the target chip detector, and determining a result of chip detection testing according to the detection time and a detection threshold selected according to a location of the target chip detector in the mechanical system and the injection location.

An embodiment apparatus includes a slurry tube having a first cavity, where the slurry tube is a clear plastic tube having an outer diameter (O.D.) between about 6 mm and 10 mm, a wall that is between about 1 mm and 2 mm thick, and a length between about 30 and 42 inches, an oil disposed in the first cavity, and a plurality of chips disposed in the oil, where chips of the plurality of chips are conductive metal chips, where the oil and the plurality of chips substantially fill the first cavity, where the first cavity is substantially free of air before use, and where each chip of the plurality of chips has a substantially same shape.

BRIEF DESCRIPTION OF THE DRAWINGS

For a more complete understanding of the present invention, and the advantages thereof, reference is now made to the following descriptions taken in conjunction with the accompanying drawings, in which:

FIG. 6A is an exterior view of the underside of an MRGB according to some embodiments;

DETAILED DESCRIPTION OF ILLUSTRATIVE EMBODIMENTS

Figure 1:
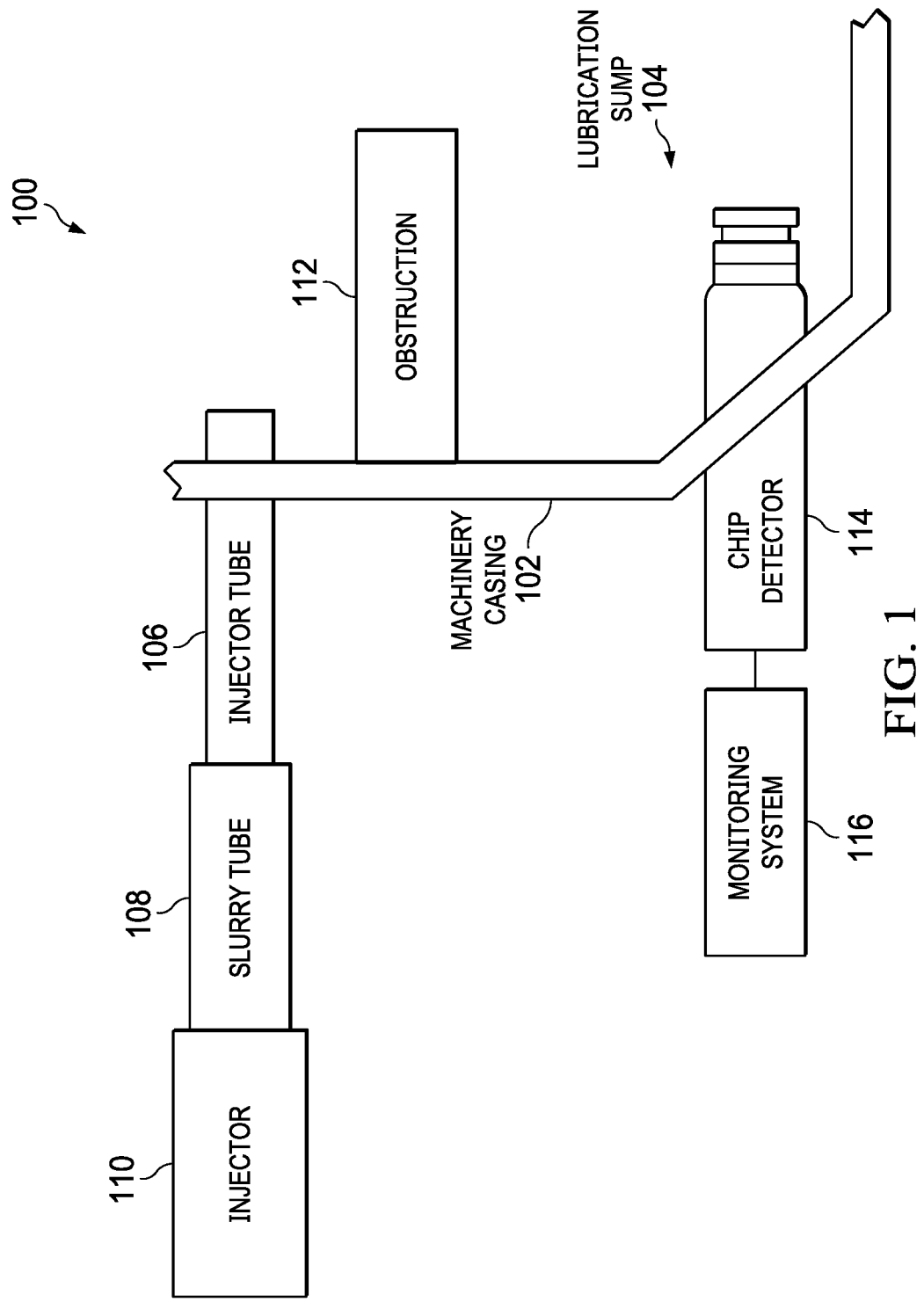
FIG. 1 is a side view of a test system according to some embodiments.

For mechanical systems, the use of complex power transmission, motion, support and fastening systems frequently requires structures that use friction generating contact points, such as metal-on-metal contact points, metal-on polymer, polymer-on-polymer, or other abrasive contact points. The friction generating contact points may be bearings, gears, friction elements, and the like. Frequently, a lubricant such as oil, transmission fluid, water, or the like, is used to lubricate friction generating contact points, and for metal-on-metal contact points in particular. Wear and failure of components results in fragments, particles or chips being generated by the parent component. Tracking the presence of chips in a mechanical system permits early detection of component failure. In systems where metal components are used as part of a friction generating contact point, the conductivity of the metal chips may be advantageously used to monitor the system for degradation.

Chip detectors may be disposed in the system to detect chips or particles by identifying the presence of conductive chips that bridge an electrical contact. The use of a lubricant in the system carries the chips away from the damaged element to a lubricant sump or lubricant collection area, and the chip detectors may be disposed in areas where lubricant and chips collect so that the chip detectors effectively detect the chips.

Embodiments of the chip detection test system provide a system and method for verifying that the arrangement of chip collectors in the system effectively detects chips or particles. The chip detection allows verification of the chip detector ability to detect ferrous or other conductive particles in an oil system, which under normal use, may indicate impending failure of a component such as a bearing or gear. A mechanical system design includes strategic locations within the gearbox for chip detectors in an effort to provide early failure detection of components. In some embodiments, an efficient method for evaluating the chip detection system includes testing while inflicting minimal residual damage on internal system components.

In some embodiments, the test includes injecting a slurry of metal particles in oil into a mechanical system such as a gearbox, while the system is running. This simulates a component failure. The injected test particles may be sized to flow through the gearbox components, and in some embodiments, may be sized to, and formed from a selected material that, permits the particles to flow through the system without damaging components or components surfaces, or lodging in recesses or on the components.

In some embodiments, the test method may include one or more runs or tests during which small quantities of steel chips are injected into a system, with the time required to activate chip detectors recorded through a data recording system and used to determine whether the chip detection system meets requirements. The test chips may be injected directly into bearings and areas with blind passages to demonstrate effectiveness of the lubrication system ability to transport particles to a chip detector when particles are introduced in worst case locations.

FIG. 1 is a side view of a test system 100 according to some embodiments. The chip detection test is performed on machinery having a chip detector 114. The chip detector 114 may be disposed in a machinery casing 102, and may extend through the machinery casing 102 to a lubrication sump 104 or other lubricant collection region or lubrication passage. In some embodiments, the chip detector 114 is a magnetic-electric chip detector having a magnet between two electrical contacts. The magnet attracts ferrous materials, or other magnetic materials, and when enough chips accumulate on the magnet, the accumulated chips bridge the electrical contacts so that an electrical connection is formed across the contacts. A monitoring system 116 such as a monitoring computer, test system, flight control computer, engine control computer (ECC), or the like, determines that the chip detector 114 has been activated. In other embodiments, the chip detector 114 is a screen-type detector with screens that act as electrical contacts and that trap conductive chips. The screen-type detector completes an electrical circuit when the screen collects enough particles to bridge between adjacent screens or to bridge across elements of a single screen.

For testing the chip detector 114, a slurry having conductive chips is introduced into the machinery casing 102. The slurry may be introduced into the machinery casing 102 so that an identified or targeted obstruction 112 is between the slurry injection location and the relevant chip detector 114. This permits the chip detector testing to verify that the design of the lubricant paths bring the lubricant past or through the targeted obstruction 112 to the relevant chip detector 114. In some embodiments, the targeted obstruction 112 may be a bearing, gear or gear set, small lubricant passage or a lateral lubricant passage, vertical lubricant return, or the like.

The slurry may be injected into the machinery casing 102 through an injector tube 106 that extends through the machinery casing 102. The slurry may be held in a slurry tube 108 connected to the injector tube 106 until it is injected into through the machinery casing 102. The slurry may be injected by an injector no that is attached to the slurry tube 108 and that pushes the slurry from the slurry tube 108 through the injector tube 106. Once injected through the machinery casing 102, the slurry moves through the targeted obstruction 112 into the lubrication sump 104 or into another area where the chip detector 114 detects the chips in the slurry.

In some embodiments, the injector tube 106 may be hollow rigid tubing that is epoxied, glued, bolted, or otherwise secured in the wall of the machinery casing 102. In some embodiments, the injector tube may be sealed against the machinery casing 102 to prevent leaks, and to maintain operating pressure within the system.

In some embodiments, the chips used for the chip detector test may be steel and substantially uniform saw cut rectangular chips that provide a shape similar to debris generated by bearing race deterioration, however larger in size. The larger size may be utilized to simulate bearing failures without inducing an actual spall resulting in bearing failure during the test. This also allows for more accurate tracking of the number of chips, determination of where chips are trapped in the gearbox, and enables thorough cleaning after each injection. The debris may be mixed with a specific quantity of oil to form the slurry for injection into the gearbox. The debris may be injected into the specific locations by the use of regulated low pressure air blown through a plastic tube containing the chip and oil slurry.

Figure 2:
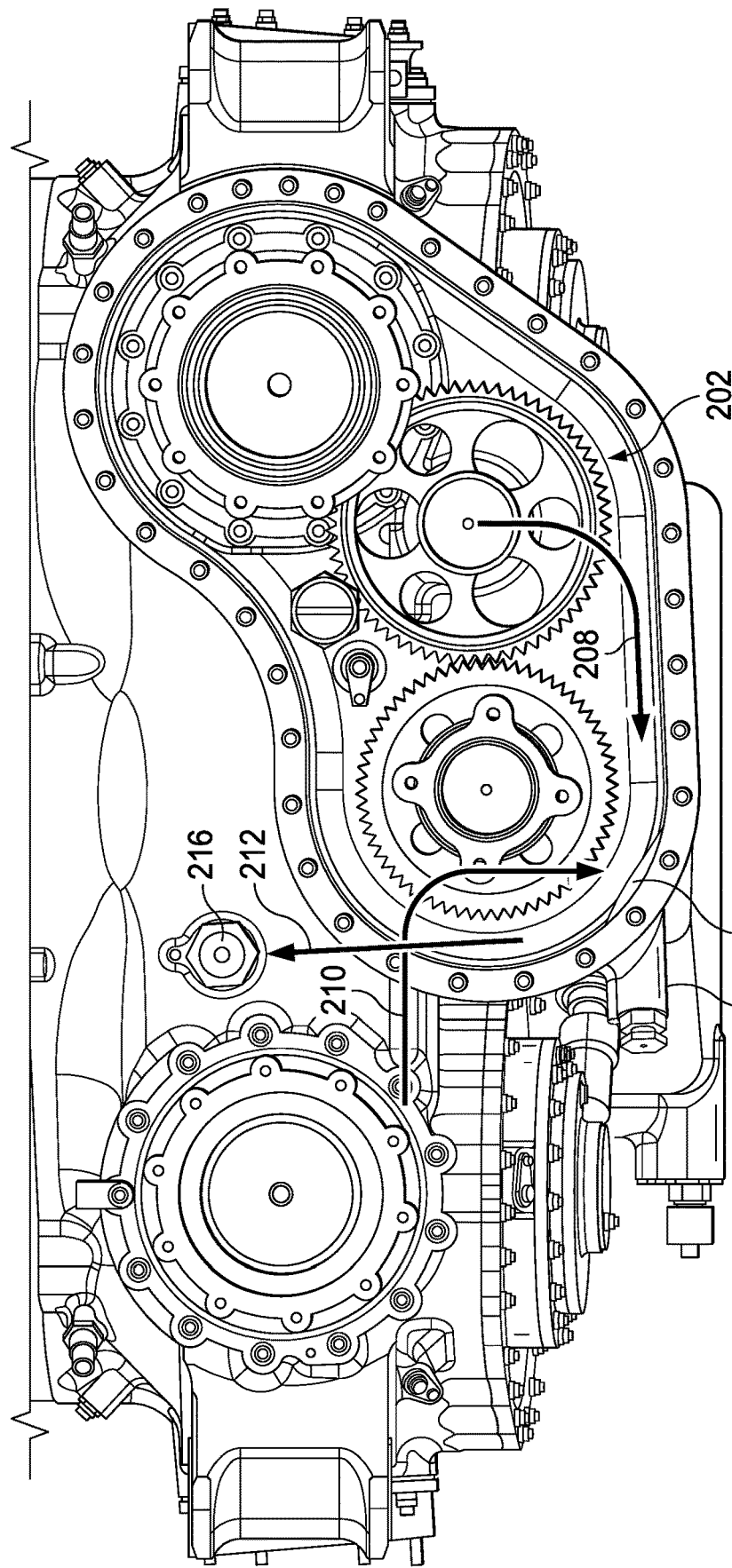
FIG. 2 is a diagram illustrating lubricant flow paths for a mechanical system according to some embodiments.

FIG. 2 is a diagram illustrating lubricant flow paths for a mechanical system according to some embodiments. The chip detection method may, in some embodiments, be performed on a mechanical system such as a main rotor gearbox (MRGB) for a rotorcraft. The gearbox may have a lubricant sump such as a tail rotor sump 202 that collects lubricant or oil that drains from an oil drain path 208 from a tail rotor gearbox section through one or more gears. A tail rotor sump chip detector 206 may extend through a case opening 204 to a sump return path 212 such as an oil scavenge path from the tail rotor sump that passes, for example, a tail rotor scavenge chip detector 216. The gearbox may also have one or more other drain paths, such as a drain path 210 from an outboard race of, for example, an input bearing. In some embodiments, the chip detector test may be performed by injecting slurry along one drain path 208 to ensure that the tail rotor sump chip detector 206 is able to accurately detect debris from the tail rotor section. Additional tests may be performed by introducing slurry along the drain path 210 and monitoring the tail rotor sump chip detector 206 or monitoring the tail rotor scavenge chip detector 216, or by introducing slurry along another drain path, such as the drain path 210 from the input bearing outboard race and monitoring the chip detectors 206, 216.

Figure 3:
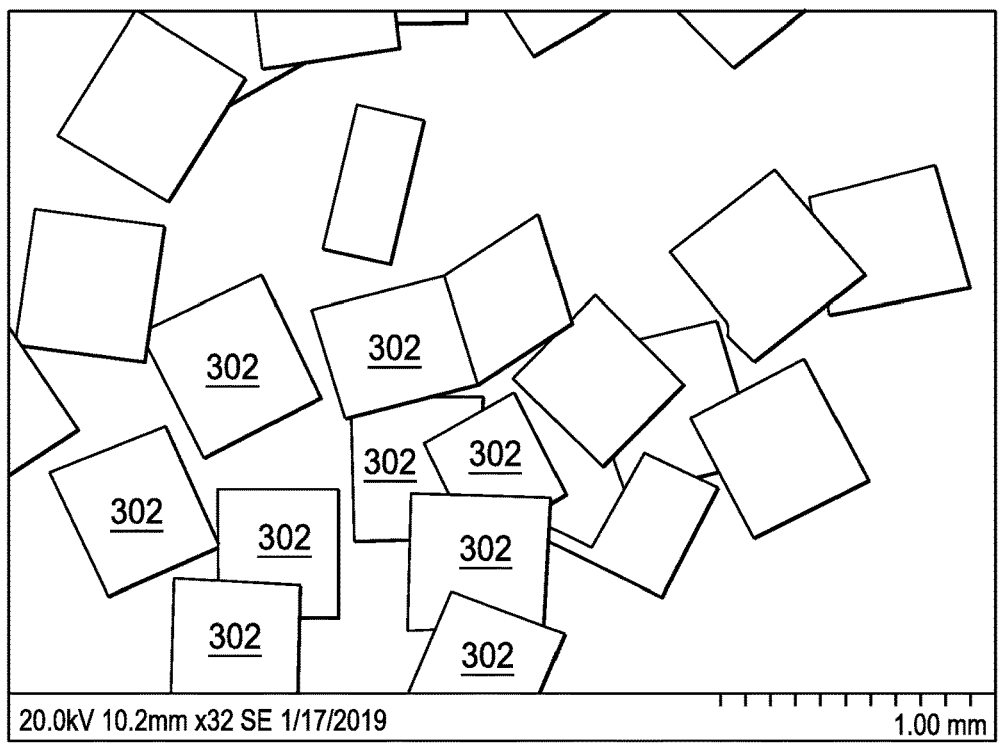
FIG. 3 is a diagram illustrating an example of chips used in an embodiment chip detector test.

FIG. 3 is a diagram illustrating an example of chips 302 used in an embodiment chip detector test. In some embodiments, chips 302 used in the slurry may be metal chips, or another conductive chip. Additionally, in some embodiments, the chips 302 may be ferromagnetic otherwise attracted to a magnet in a chip detector. The chips 302 may each have a substantially similar shape and may be substantially rectangular cuboids, or may be cubic. The rectangular cuboid shape may be a prism shape where the majority of the faces of the chip are rectangular or substantially rectangular. The rectangular cuboid shape has been discovered to flow through obstructions such as gears and bearing, without getting trapped in the obstruction and by allowing the chips to flow through lubricant drain paths. In some embodiments, the chips 302 used for chip detection are saw cut manufactured chips, rectangular in shape and having a size between about 475 microns and about 650 microns, and in some embodiments, the chips are about 500 microns. In some embodiments, the average size of the chips 302 is about 570 micrometers, and a total weight of the chips injected was 0.2 grams. These sizes of chips have been determined to simulate actual metallic bearing failure debris.

In some embodiments, the material for the chips 302 is selected to be a conductive metal with hardness that is lower than surfaces or faces of machinery elements such a bearings, bearing races, gears, and the like. In some embodiments, the gears and bearings may be made from a hardened steel such as M50 NiL bearing steel or the like, and the chips 302 may be a softer steel such as a low carbon or a stainless steel such as a 1000 series steel. The M50 NiL bearing steel has a Rockwell C hardness (HRC) around 61, while the 1000 series steel has a Rockwell C hardness around 19. The softer material used for the chip 302 ensures that the chips 302, if caught in a machinery element or obstruction, deform before the gear or bearing of the machinery element, so that the chips 302 are damaged or deformed rather than elements of the machinery itself. This results in the ability to perform in non-destructive testing of the machinery even in cases where the chips 302 are caught in the obstruction or other machinery element. Additionally, the regular rectangular cuboid shape permits the chips to be analyzed to determine whether the chips 302 have been damaged and determine a cause of the chip damage.

Figure 4:
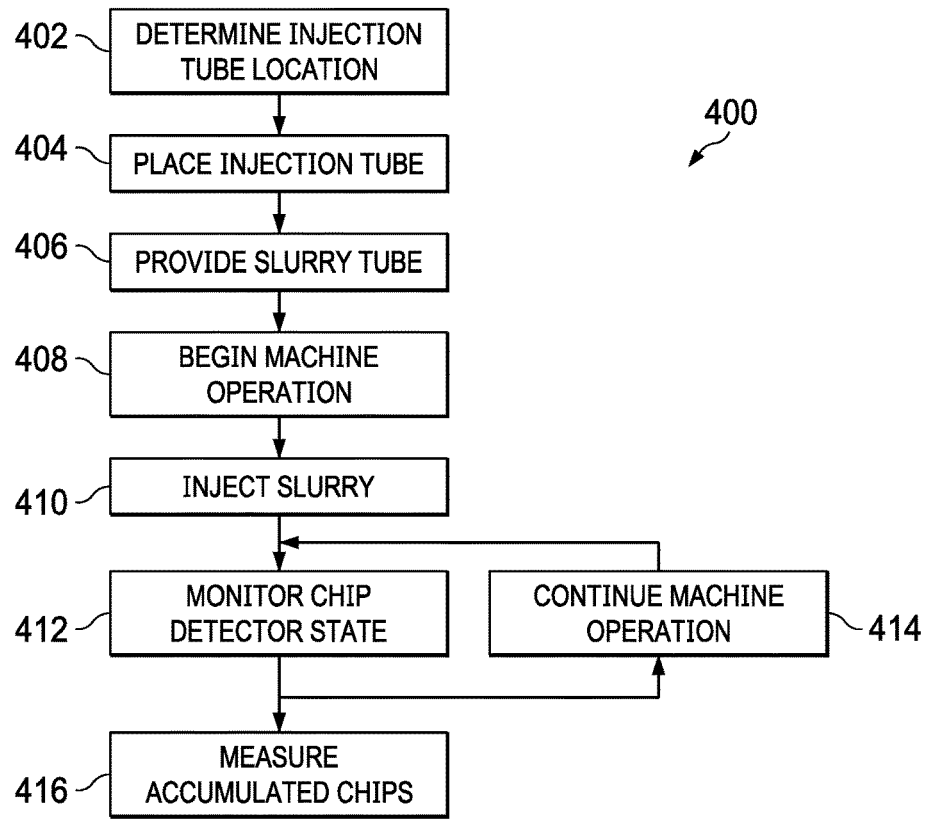
FIG. 4 is a diagram illustrating a method of performing a chip detection test according to some embodiments.

FIG. 4 is a diagram illustrating a method 400 of performing a chip detection test according to some embodiments. In block 402, an injection tube location is determined. In some embodiments, locations of injection are determined by drive system engineering based on the gearbox drain paths and the oil scavenge system. For example, the injection locations may be chosen according to a bearing or gear location that is the farthest distance from the chip detector or sump, most difficult locations for drain back, such as blind areas behind bearings where the chips must flow back through a bearing or gear to drain, very small oil return passages with minimal slope, or parts of the scavenge system that require oil to travel upward before reaching the chip detector or a lubrication scavenge section. In some embodiments, a targeted obstruction may be identified for testing, and the location for injection selected to ensure that the slurry encounters the targeted obstruction.

In block 404, the injection tube is placed in the machinery casing. Once the injection location has been determined, an opening in the machinery casing is provided. In some embodiments, the case material is drilled for the installation of injection tube, and in other embodiments, the opening may be provides by removing or drilling an inspection port, cap, door, or other movable or removable port covering or the like. The injection tube may, in some embodiments, be 0.250 inch diameter copper tubing cut to a length sufficient to attach slurry tubing on the external side of the machinery casing. The injection tube may be bent or directed in the internal side of the machinery casing to deliver the slurry to an intended location. In some embodiments, the injection tube may be secured in the opening of the machinery casing using an adhesive such as an aluminum filled epoxy adhesive to adhere the tubing to the housing and seal the tubing to the casing to minimize oil leakage.

In block 406, a slurry tube is provided. The chips may be disposed in a cavity of a slurry tube such as a clear plastic tube with a measured amount of oil or other lubricant. The slurry tube may be attached at one end to a regulated air pressure source and connected to the injection tube at the other end.

The chips may be disposed in a fluid compatible with the machinery, such as a transmission fluid, hydraulic fluid, lubricating oil, or the like, for a transmission, gear train or main rotor gearbox or the like on a rotorcraft. In some embodiments, one cubic inch ($in^3$) of oil may be provided in the slurry tube, and the chips may be disposed in the oil. In some embodiments, the slurry tube is a clear tube to permit an operator to verify that all of the slurry, including oil and chips, are properly introduced into the machinery casing. In some embodiments, the slurry tube is clear plastic tubing that is oil resistant and with an outer diameter (O.D.) between about 6-10 mm, a wall that is between about a 1-2 mm thick, and a length between about 30 and 42 inches so that the slurry tube holds the selected volume of oil and chips and is substantially free of air. In some embodiments, the slurry tube has about an 8 mm outer diameter (O.D.), about a 1.5 mm thick wall, and is about 36" long. In some embodiments, the slurry tube may be provided separately from the injection tube, or multiple slurry tubes may be prepared separately from the injection system and injection tube. The slurry tube may be provided in a sealed state, with each end capped or otherwise sealed for transportation.

In block 408, the machinery is operated normally. In some embodiments, the machinery is disposed in a test stand, and a simulated mechanical input may be applied until the machinery achieves one or more predetermined operating parameters such as a rotational speed, a normal operating pressure or a normal operating temperature. In some embodiments, for a rotorcraft MRGB, no specific torque is applied during testing, as torque may not be expected to influence the movement of chips within the MRGB. The machinery may be operated at a normal speed and allowed to reach a normal operating parameter such as a normal operating oil temperature or pressure. In an embodiment where the machinery is an MRGB, the MRGB may be brought to full rotational speed until the oil temperature reaches between about 100° F. and about 230° F. and the oil pressure reaches between about 55 pounds per square inch (psi) and about 58 psi.

In block 410, the slurry is injected into the machinery. In some embodiments, the slurry is injected using an injector such as a regulated air source, a piston, a valve, or the like. For example, the injector may be an air source configured to provide air at a regulated pressure controlled by an electrically controlled solenoid valve wired to a remote location controlled by a test stand operator, or by an automated or manual system. The air source may provide air from one end of the slurry tube at a pressure, in some embodiments, between about 10 psi and about 40 psi, and in other embodiments, at a pressure between about 20 psi and about 30 psi. The 20-30 psi range has been determined to thoroughly clear the slurry from the slurry tube without blowing air past the slurry in the slurry tube and leaving oil and chips in the slurry tube. Thorough clearing of the slurry tube permits introduction of the whole, known amount of chips into the machinery casing so that the chips may be tracked and accurately accounted for after the testing.

In block 412, the state of one or more chip detectors is monitored. In some embodiments, a monitoring system may be used to determine whether a chip detector properly detects the chips injected into the machinery. The testing may continue with continuous monitoring of the chip detector in block 412 and continued machinery operation in block 414 until or more chip detectors under test indicate detection of the chips, or until a predetermined time has passed. The duration required to trip the chip detector is recorded. The time taken after injection of the chips to receive a chip indication may be used to determine whether the chip detection capabilities of the system meet requirements, and may be compared to a predetermined detection threshold. In some embodiments, a chip indication may be received within between about 5 seconds and about 3 minutes. A detection threshold may be determined according to the geometry or length of an oil drain path, obstructions through which the slurry passes before reaching the chip detector, or the like. Additionally, when multiple tests are performed separately or simultaneously, a different detection threshold may be applied to each chip detector. In some embodiments, chip detection within the detection threshold may indicate successful chip detection testing, while not achieving chip detection within the detection threshold, may indicate failure of the chip detection testing When the testing is concluded, the state of the machinery may be analyzed, and the analysis may include measurement of the accumulated chips in block 416. In some embodiments, following the chip indication or test termination, the test stand may be shut down and chip detector removed for visual verification of media capture. In some embodiments, the chips may be cleared from the machinery, and the amount of chips disposed on the chip collectors may be analyzed to determine the effectiveness of the oil drain paths and chip detectors. In some embodiments, the chip detectors may be inspected, and the MRGB disassembled to locate, record any drain path restrictions, and remove any other remaining chips. Additionally, after testing, the gearbox or machinery may be removed from the test stand and disassembled to determine possible locations of residual chips internal to the gearbox to further evaluate obstructions which may prevent timely chip indications. The machinery may then be thoroughly cleaned before re-assembly to prevent false indications during subsequent tests.

In some embodiments, testing may be performed at multiple injection locations to verify the engineering of multiple oil drain paths and efficacy of multiple chip detectors. For example, in an MRGB for a rotorcraft, multiple tests may be used to determine that a variety of chip detectors are able to each effectively detect chips or other debris in an associated oil drain path. In some embodiments, chip detection verification testing may be performed on a tail rotor drive section, an input pinion, a gearshaft quill, a bullgear upper roller, an upper planetary gearset, and an upper mast bearing.

Figure 5A:
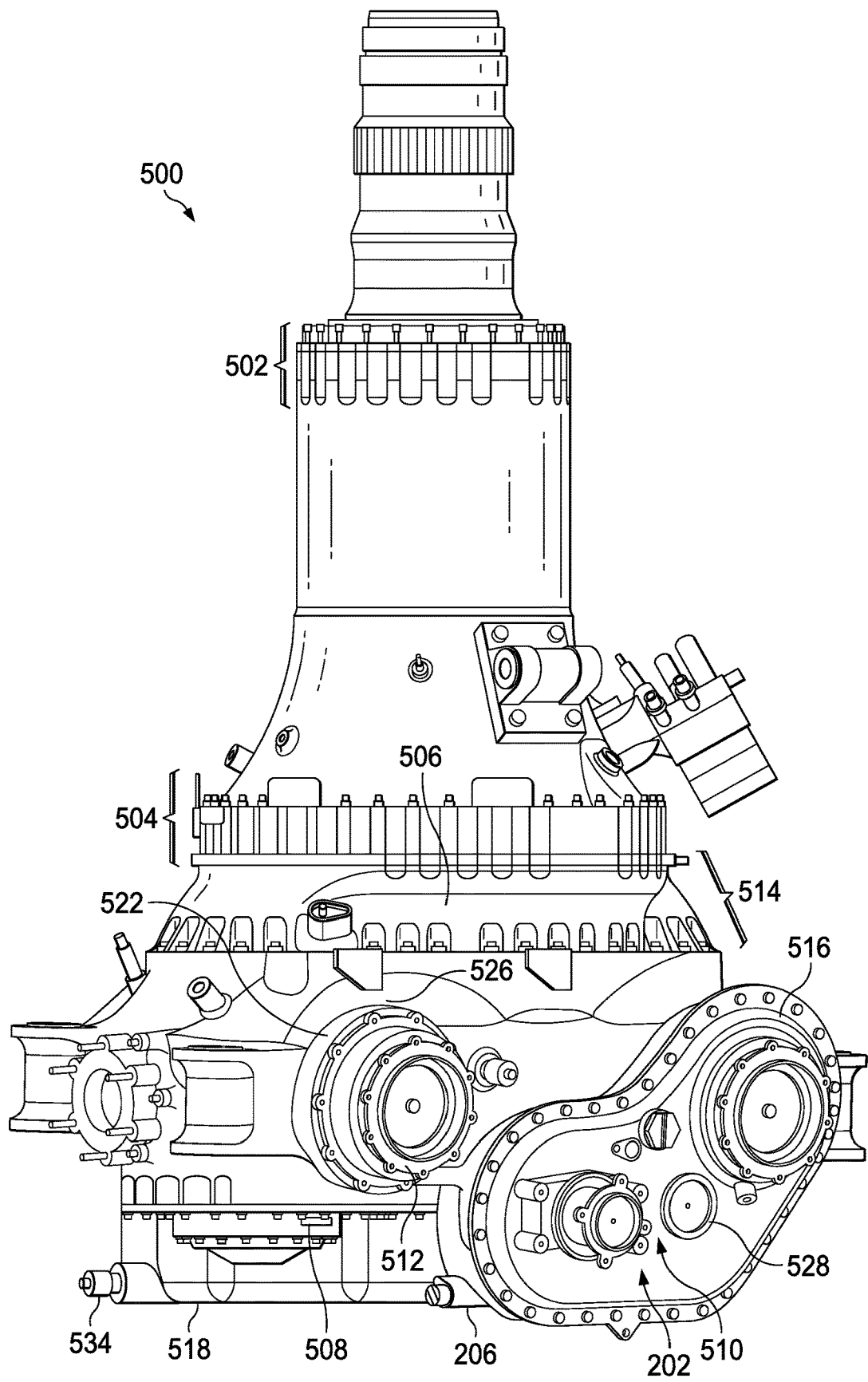
FIGS. 5A and 5B illustrate a rotorcraft main rotor gearbox (MRGB) according to some embodiments.
Figure 5B:
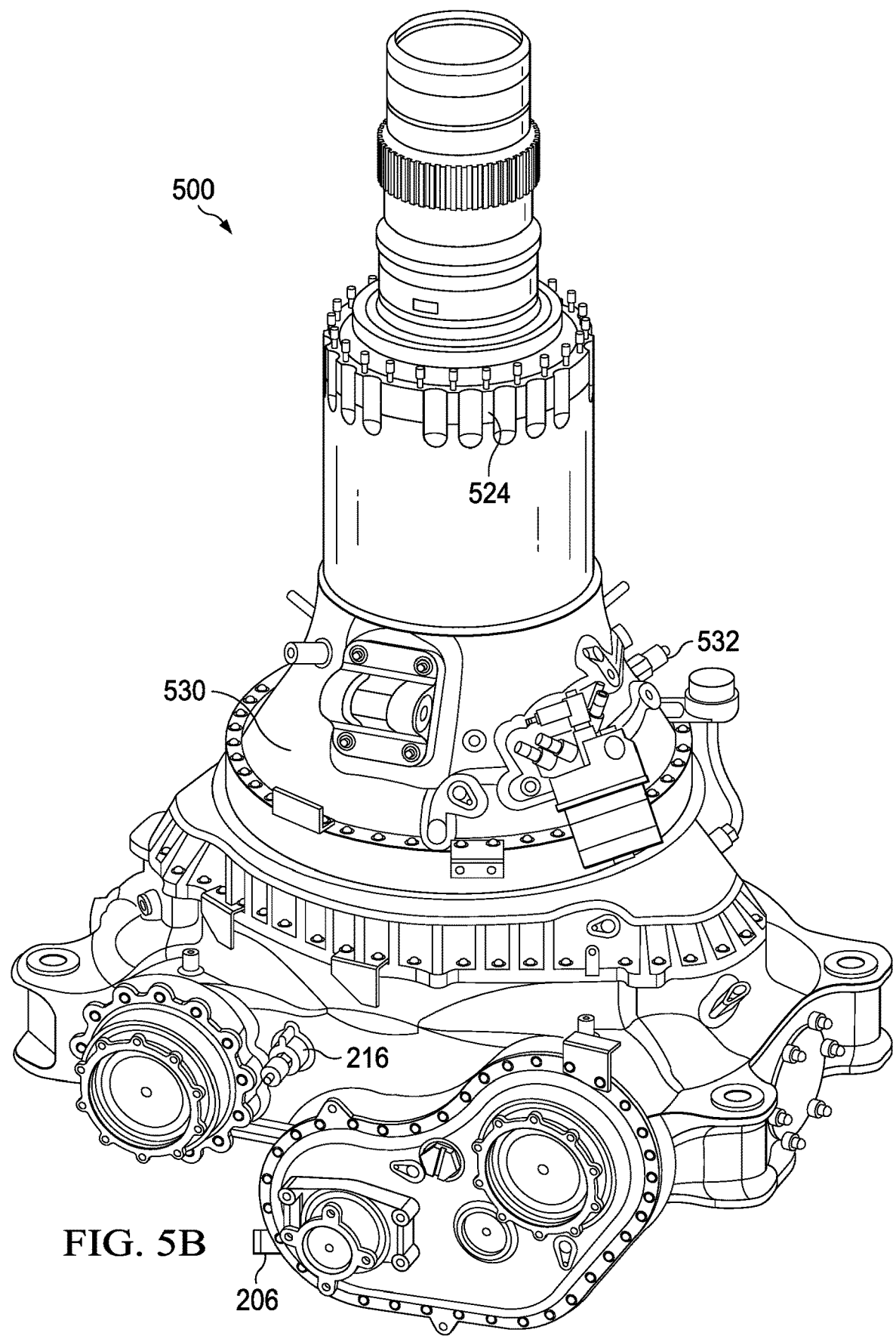

FIGS. 5A and 5B illustrate an MRGB 500 according to some embodiments. FIG. 5A is a first view of the MRGB 500 and FIG. 5B is a second view of the MRGB 500, and the first and second views are referenced together below. In some embodiments, the MRGB 500 may have a main sump 518 that collects oil from the main rotor mechanical system, and the main sump chip detector 534 may be disposed in the main sump 518 for detection of chips. In some embodiments, the MRGB 500 also has a lower gearshaft section 508 housing lower gearshaft bearings that may be duplex and roller bearings supporting a gearshaft quill.

The MRGB 500 may have a tail rotor drive section 510 with a tail rotor drive section cover 516 covering a gearset that drives the tail rotor, as shown in FIG. 2, above. A tail rotor drive section injection location 528 is disposed in the tail rotor drive section cover 516. In some embodiments, the tail rotor drive section injection location 528 may be an opening in an inspection plug disposed on the tail rotor drive section cover 516 at a targeted obstruction such as a selected gear in the tail rotor drive gearset. The tail rotor sump chip detector 206 may be disposed in a tail rotor sump 202, and may be associated with, and monitor for chips injected through, the tail rotor drive section injection location 528.

Additionally, the MRGB may have an input pinion section 512 with, for example, a triplex bearing, and a input pinion injection location 522 may be located in, for example, a casing or housing for a bearing of an input pinion gear in the input pinion section 512. The input pinion injection location 522 provides an opening for injection of chip or slurry into the input pinion section 512 and permits selection of the input pinion bearing as a targeted obstruction. The tail rotor sump chip detector 206 and tail rotor scavenge chip detector 216 may each be associated with, and monitor for chips injected through the input pinion injection location 522.

The MRGB 500 may further have a planetary pinion region 504 and a MRGB mid-case section 514 having a bullgear upper roller bearing region 506. A bullgear roller injection location 526 and an upper planetary chip injection location 530 may be disposed in the casing of the MRGB 500. The upper planetary chip injection location 530 permits injection of chips or slurry into planetary pinions of a planetary gearset in the planetary pinion region 504. A mid-case/planetary chip detector (element 702, FIG. 7, below) may be disposed in the MRGB mid-case section to detect chips or debris generated by, or injected to, elements in a planetary gear set such as such as upper planetary pinion gears, pinion bearings, or associated elements. Thus, the mid-case/planetary chip detector (element 702, FIG. 7) may be associated with, and monitor for chips injected through the upper planetary chip injection location 530.

The MRGB 500 may have an upper mast roller bearing region 502 housing an upper mast roller bearing and having a upper mast chip injection location 524 permitting injection of chip or slurry into the upper mast roller bearing in the upper mast roller being region 502. An upper mast chip detector 532 may be disposed in the casing of the MRGB 500 and may be situated to detect chips or debris generated by, or injected to, case section to detect chips or debris generated by, or injected to, elements in the upper mast roller bearing region 502 such as the mast, upper mast roller bearing, or associated elements. The upper mast chip detector 532 may be associated with, and monitor for chips injected through the upper mast chip injection location 524.

FIG. 6A is an exterior view of the underside of an MRGB 500 according to some embodiments. The MRGB 500 may, in some embodiments, have a gearshaft quill region 602 with a gearshaft quill injection location 620 disposed in the mechanical system. Slurry from the gearshaft quill region 602 may drain into the main sump 518, and may be monitored by the main sump chip detector 534.

Figure 6B:
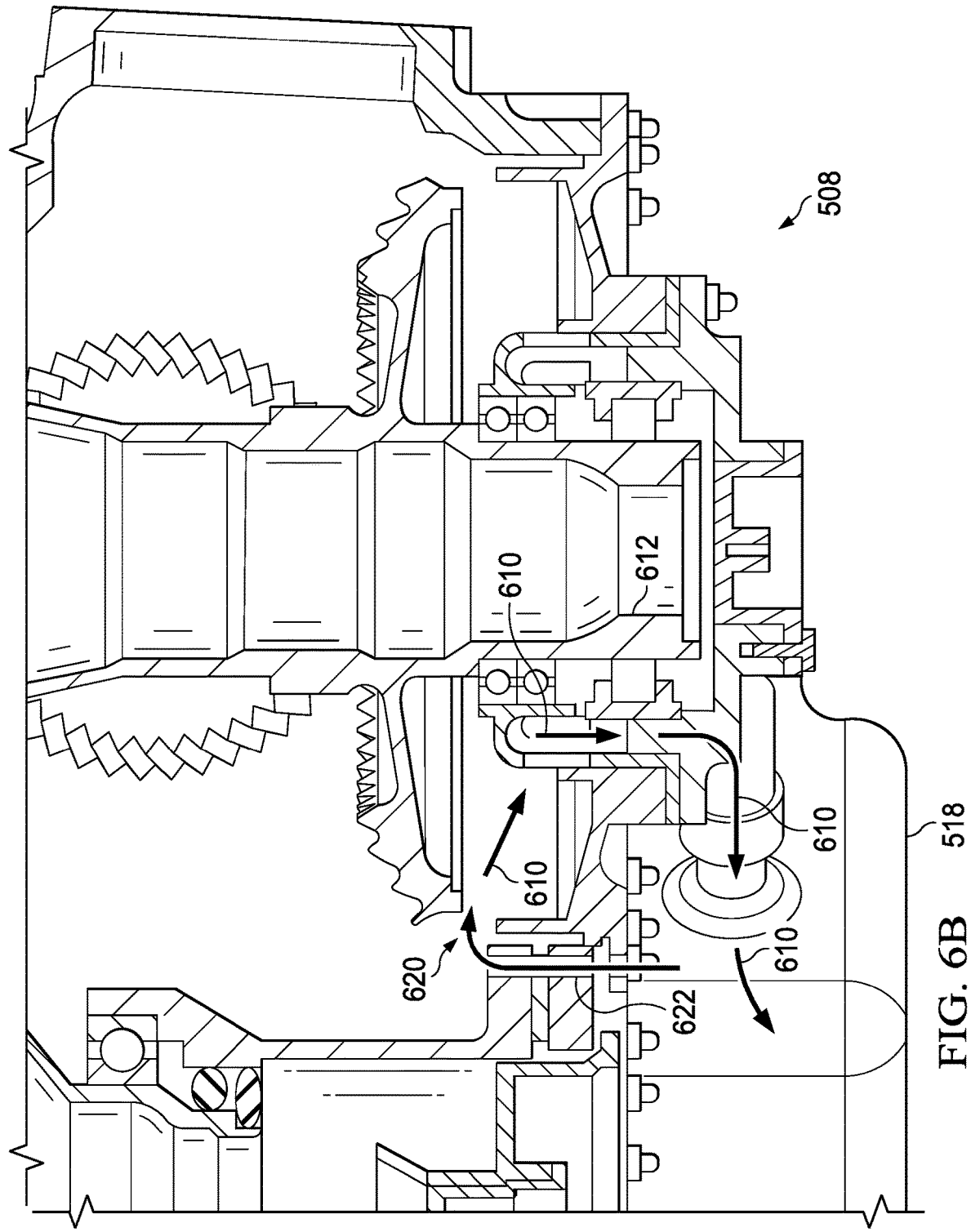
FIG. 6B is a cutaway view of a MRGB lower gearshaft section and illustrates a gearshaft quill according to some embodiments.

FIG. 6B is a cutaway view of a MRGB lower gearshaft section 508 and illustrates a gearshaft quill 612 according to some embodiments. A gearshaft quill injection tube 622 may be provided at the gearshaft quill injection location 62o. In some embodiments, the gearshaft quill injection tube 622 may be bent or otherwise configure to deliver chips or slurry to a specific location within the MRGB casing. The gearshaft quill injection tube 622 provides the chips to an oil drain path 610 through a bearing or housing supporting the gearshaft quill 612. In some embodiments, the bearing or housing for the gearshaft quill 612 is a targeted obstruction, and the oil drain path 610 allows the slurry to flow through the targeted obstruction, and return to the main sump 518 where the main sump chip detector 534 detects chip in the slurry. Thus, the testing at gearshaft quill injection location 620 test for detection of debris generated at the gearshaft quill region 602 by, for example, the gearshaft quill 612, the bearing or housing for the gearshaft quill 612, or an associated element. Thus, the main sump chip detector 534 may be associated with, and monitor for chips injected through, the gearshaft quill injection location 620.

Figure 7A:
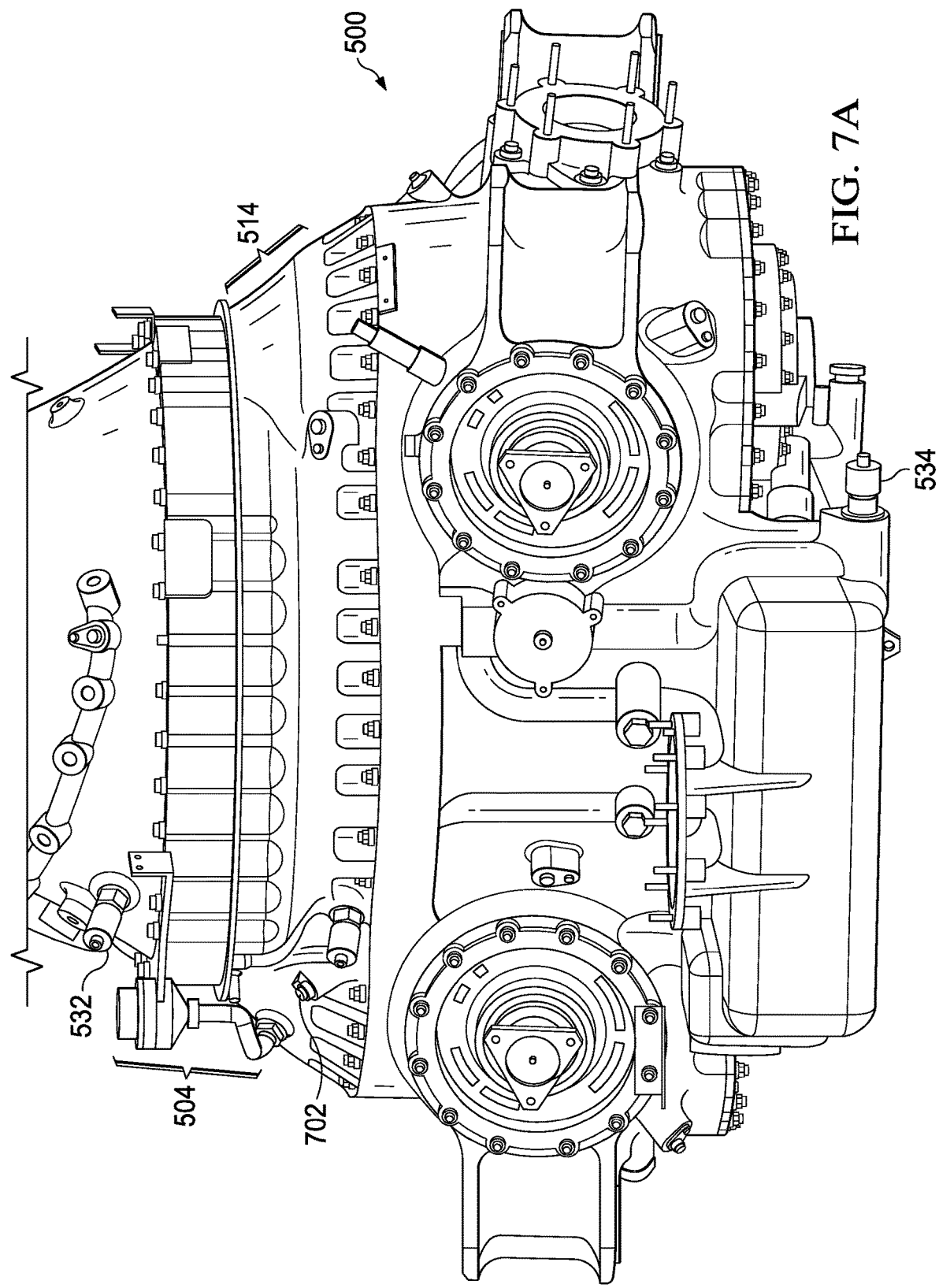
FIG. 7A is an exterior view of the backside of the MRGB according to some embodiments.

FIG. 7A is an exterior view of the backside of the MRGB 500 according to some embodiments. The MRGB 50*o* has a mid-case/planetary chip detector 702 disposed in the mid-case section 514 and below the planetary pinion region 504.

Figure 7B:
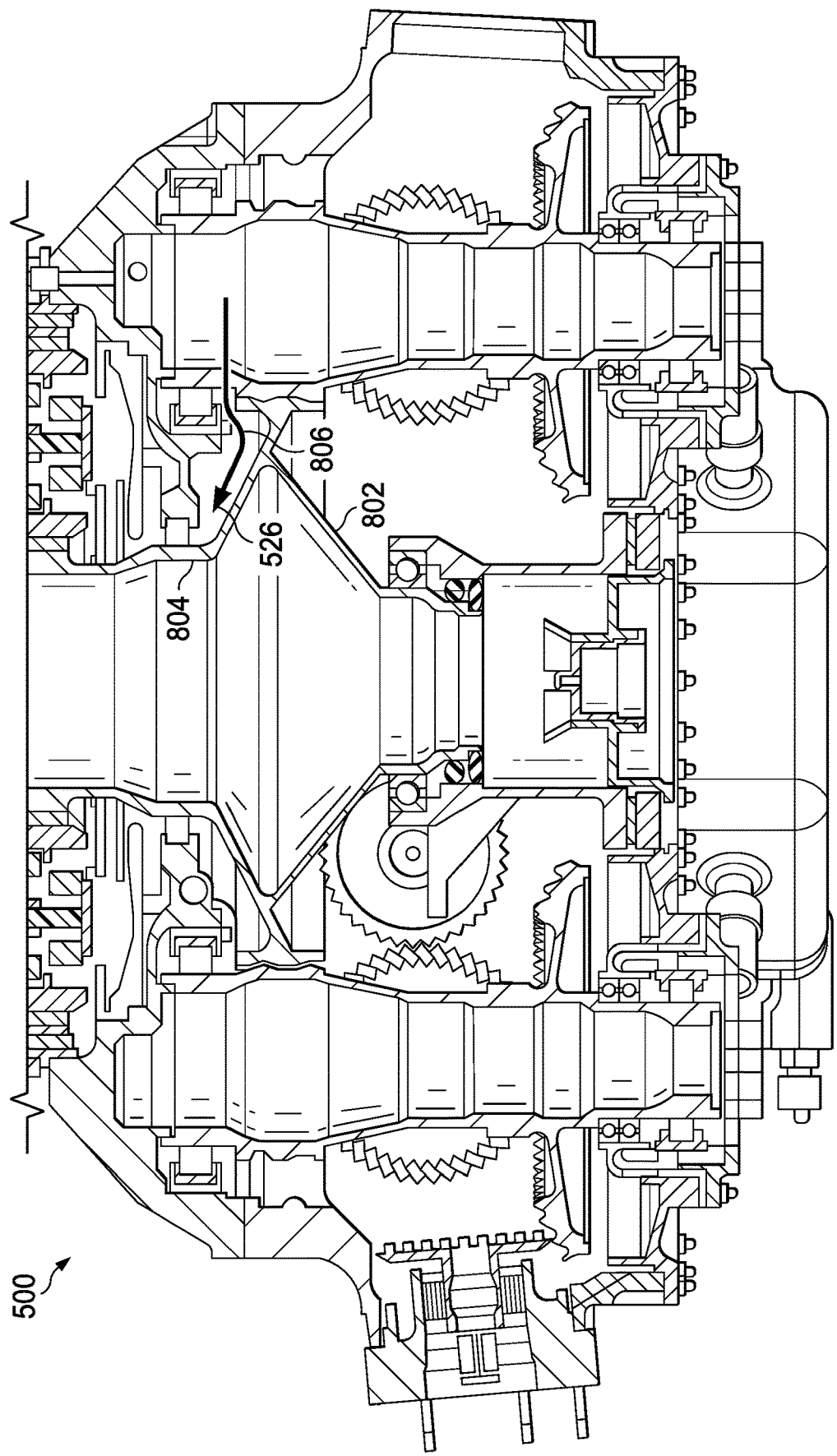
FIG. 7B is a cutaway view of the MRGB lower gearshaft section and illustrates a bullgear according to some embodiments.

FIG. 7B is a cutaway view of the MRGB lower gearshaft section 508 and illustrates a bullgear 802 according to some embodiments. In some embodiments, bullgear injection tube 806 may be bent or otherwise configure to deliver chips or slurry through the bullgear roller injection location 526 near the bullgear 802 and, for example, a bullgear upper roller journal 804. The mid-case/planetary chip detector 702 may detect chips or debris generated by, or injected to, the bullgear 802 or associated elements. Thus, the mid-case/planetary chip detector 702 may be associated with, and monitor for chips injected through the bullgear roller injection location 526.

An embodiment method includes determining a slurry injection location in machinery according to a targeted obstruction in the machinery in relation to a target chip detector of the machinery, placing an injection tube through a machinery casing of the machinery, providing a slurry tube connected to the injection tube, the slurry tube containing a slurry comprising conductive chips and a lubricant, operating the machinery until the machinery meets one or more predetermined operating parameters, injecting the slurry into the machinery casing during operation of the machinery and after the machinery meets the one or more predetermined operating parameters, and monitoring the target chip detector for detection of the conductive chips during the operation of the machinery.

In some embodiments, the lubricant is an oil, and each chip of the conductive chips has a substantially rectangular cuboid shape, and each chip of the conductive chips is steel and has a size between about 475 microns and about 650 microns. In some embodiments, each chip of the conductive chips has a hardness that is less than a hardness of at least the targeted obstruction. In some embodiments, the injecting the slurry includes using an injector to provide regulated air that forces the slurry into the casing. In some embodiments, the regulated air is provided at a pressure between about 10 pounds per square inch (psi) and about 40 psi. In some embodiments, the determining the slurry injection location includes identifying the targeted obstruction for testing, and selecting the slurry injection location to cause the slurry to encounter the targeted obstruction. In some embodiments, the method further includes determining a detection time that is a time between injection of the conductive chips and detection of one or more of the conductive chips by the target chip detector, and determining a result of chip detection testing according to the detection time and a detection threshold selected according to a location of the target chip detector in the machinery and the slurry injection location.

An embodiment method includes injecting conductive chips into a mechanical system at an injection location in the mechanical system during operation of the mechanical system and when the mechanical system is at a normal operating parameter, monitoring a target chip detector of the mechanical system for detection of the conductive chips during operation of the mechanical system, determining a detection time that is a time between injection of the conductive chips and detection of one or more of the conductive chips by the target chip detector, and determining a result of chip detection testing according to the detection time and a detection threshold selected according to a location of the target chip detector in the mechanical system and the injection location.

In some embodiments, the injection location in the mechanical system is determined according to a targeted obstruction in the mechanical system in relation to a target chip detector of the mechanical system, and the method further includes providing a slurry tube having a slurry disposed therein, the slurry comprising the conductive chips and an oil, and where the injecting the conductive chips includes injecting the slurry through a casing of the mechanical system using a regulated air source. In some embodiments, each chip of the conductive chips has a substantially rectangular cuboid shape, and each chip of the conductive chips is steel and has a size between about 475 microns and about 650 microns. In some embodiments, each chip of the conductive chips has a hardness that is less than a hardness of at least the targeted obstruction. In some embodiments, the regulated air source provides air for injection at a pressure between about 10 pounds per square inch (psi) and about 40 psi. In some embodiments, the mechanical system is a main rotor gearbox for a rotorcraft. In some embodiments, the method is performed on at least one of a tail rotor drive section, an input pinion, a gearshaft quill, a bullgear upper roller, an upper planetary gearset, or an upper mast bearing of the main rotor gearbox.

An embodiment apparatus includes a slurry tube having a first cavity, where the slurry tube is a clear plastic tube having an outer diameter (O.D.) between about 6 mm and 10 mm, a wall that is between about 1 mm and 2 mm thick, and a length between about 30 and 42 inches, an oil disposed in the first cavity, and a plurality of chips disposed in the oil, where chips of the plurality of chips are conductive metal chips, where the oil and the plurality of chips substantially fill the first cavity, where the first cavity is substantially free of air before use, and where each chip of the plurality of chips has a substantially same shape.

In some embodiments, the apparatus further includes an injection tube, where the injection tube is a rigid tube having a second cavity, and an injector configured to provide air at a regulated pressure. In some embodiments, the injection tube extends through a casing of a machinery, a first end of the injection tube is disposed at injection location associated with a targeted obstruction, a first end of the slurry tube is connected to the injector, a second end of the slurry tube is connected to a second end of the injection tube, and the first cavity is contiguous with the second cavity. In some embodiments, the apparatus further includes a monitoring system connected to a chip detector of the machinery and configured to determine detection, by the chip detector, of an accumulation of one or more chips of the plurality of chips at the chip detector. In some embodiments, each chip of the plurality of chips has a substantially rectangular cuboid shape. In some embodiments, each chip of the plurality of chips is steel and has a size between about 475 microns and about 650 microns.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description.

It is therefore intended that the appended claims encompass any such modifications or embodiments.

What is claimed is:

1. A method, comprising:
   determining a slurry injection location in machinery according to a targeted obstruction in the machinery in relation to a target chip detector of the machinery;
   placing an injection tube through a machinery casing of the machinery;
   providing a slurry tube connected to the injection tube, the slurry tube containing a slurry comprising conductive chips and a lubricant;
   operating the machinery until the machinery meets one or more predetermined operating parameters;
   injecting the slurry into the machinery casing during operation of the machinery and after the machinery meets the one or more predetermined operating parameters; and
   monitoring the target chip detector for detection of the conductive chips during the operation of the machinery.

2. The method of claim 1, wherein the lubricant is an oil, and wherein each chip of the conductive chips has a substantially rectangular cuboid shape, and wherein each chip of the conductive chips is steel and has a size between about 475 microns and about 650 microns.

3. The method of claim 2, wherein each chip of the conductive chips has a hardness that is less than a hardness of at least the targeted obstruction.

4. The method of claim 1, wherein the injecting the slurry comprises using an injector to provide regulated air that forces the slurry into the casing.

5. The method of claim 4, wherein the regulated air is provided at a pressure between about 10 pounds per square inch (psi) and about 40 psi.

6. The method of claim 1, wherein the determining the slurry injection location comprises identifying the targeted obstruction for testing, and selecting the slurry injection location to cause the slurry to encounter the targeted obstruction.

7. The method of claim 1, further comprising determining a detection time that is a time between injection of the conductive chips and detection of one or more of the conductive chips by the target chip detector; and
   determining a result of chip detection testing according to the detection time and a detection threshold selected according to a location of the target chip detector in the machinery and the slurry injection location.

8. A method, comprising:
   injecting conductive chips into a mechanical system at an injection location in the mechanical system during operation of the mechanical system and when the mechanical system is at a normal operating parameter;
   monitoring a target chip detector of the mechanical system for detection of the conductive chips during operation of the mechanical system;
   determining a detection time that is a time between injection of the conductive chips and detection of one or more of the conductive chips by the target chip detector; and
   determining a result of chip detection testing according to the detection time and a detection threshold selected according to a location of the target chip detector in the mechanical system and the injection location.

9. The method of claim 8, wherein the injection location in the mechanical system is determined according to a targeted obstruction in the mechanical system in relation to a target chip detector of the mechanical system;
   wherein the method further comprises providing a slurry tube having a slurry disposed therein, the slurry comprising the conductive chips and an oil; and
   wherein the injecting the conductive chips comprises injecting the slurry through a casing of the mechanical system using a regulated air source.

10. The method of claim 9, wherein each chip of the conductive chips has a substantially rectangular cuboid shape, and wherein each chip of the conductive chips is steel and has a size between about 475 microns and about 650 microns.

11. The method of claim 10, wherein each chip of the conductive chips has a hardness that is less than a hardness of at least the targeted obstruction.

12. The method of claim 9, wherein the regulated air source provides air for injection at a pressure between about 10 pounds per square inch (psi) and about 40 psi.

13. The method of claim 8, wherein the mechanical system is a main rotor gearbox for a rotorcraft.

14. The method of claim 13, wherein the method is performed on at least one of a tail rotor drive section, an input pinion, a gearshaft quill, a bullgear upper roller, an upper planetary gearset, or an upper mast bearing of the main rotor gearbox.

15. An apparatus, comprising:
   an injection tube extending through a machinery casing of a machinery at a location associated with to a targeted obstruction in the machinery in relation to a target chip detector of the machinery;
   an injector configured to provide air at a regulated pressure;
   a slurry tube having a first cavity, wherein the slurry tube is a clear plastic tube having an outer diameter (O.D.) between about 6 mm and 10 mm, a wall that is between about 1 mm and 2 mm thick, and a length between about 30 and 42 inches, wherein a first end of the slurry tube is configured to be connected to the injector, and wherein a second end of the slurry tube is connected to the injector;
   an oil disposed in the first cavity; and
   a plurality of chips disposed in the oil, wherein chips of the plurality of chips are conductive metal chips, wherein the oil and the plurality of chips substantially fill the first cavity and wherein the first cavity is substantially free of air before use, and wherein each chip of the plurality of chips has a substantially same shape;
   wherein the injector is configured to inject the slurry into the machinery casing during operation of the machinery and after the machinery meets the one or more predetermined operating parameters such that detection of the conductive metal chips by the target chip detector during the operation of the machinery may be monitored.

16. The apparatus of claim 15,
   wherein the injection tube is a rigid tube having a second cavity.

17. The apparatus of claim 16,
   wherein the first cavity is contiguous with the second cavity.

18. The apparatus of claim 17, further comprising a monitoring system connected to a chip detector of the machinery and configured to determine detection, by the chip detector, of an accumulation of one or more chips of the plurality of chips at the chip detector.

19. The apparatus of claim 15, wherein each chip of the plurality of chips has a substantially rectangular cuboid shape.

20. The apparatus of claim 19, wherein each chip of the plurality of chips is steel and has a size between about 475 microns and about 650 microns.

\* \* \* \* \*